United States Patent [19]

Pfeiffer

[11] 4,386,075
[45] May 31, 1983

[54] RENALLY ACTIVE TETRAPEPTIDES
[75] Inventor: Francis R. Pfeiffer, Cinnaminson, N.J.
[73] Assignee: SmithKline Beckman Corporation, Philadelphia, Pa.
[21] Appl. No.: 359,958
[22] Filed: Mar. 19, 1982

Related U.S. Application Data
[63] Continuation-in-part of Ser. No. 349,448, Feb. 17, 1982.
[51] Int. Cl.³ ............................................. A61K 37/00
[52] U.S. Cl. ................................................... 424/177
[58] Field of Search .......................................... 424/177

[56] References Cited
FOREIGN PATENT DOCUMENTS
2943582  5/1980  Fed. Rep. of Germany ...... 424/177

*Primary Examiner*—Delbert R. Phillips
*Attorney, Agent, or Firm*—William H. Edgerton; Richard D. Foggio; Alan D. Lourie

[57] ABSTRACT

N-Acyltetrapeptides are described which are active in improving renal function. An exemplary species is N-4-(4-hydroxyphenyl)-butyryl-L-prolyl-D,L-α-methyl-phenylalanyl-glycyl-L-proline.

12 Claims, No Drawings

RENALLY ACTIVE TETRAPEPTIDES

This application is a continuation-in-part of U.S. patent application Ser. No. 349,448 filed Feb. 17, 1982.

This invention comprises a new group of chemical compounds whose structures are characterized by having a tetrapeptide chain with terminal prolyl groups. The tetrapeptides have pharmacodynamic activity especially useful for improving renal function.

DESCRIPTION OF THE ART

I am not aware of any prior publications material to the compounds and utilities described hereafter. In my copending earlier filed applications, (Ser. No. 300,546 filed Sept. 9, 1981 and Ser. No. 318,721 filed Nov. 6, 1981), a number of related di- and tripeptides are claimed. Certain prior literature references are discussed therein.

The present compounds are distinguished from those of my prior applications since these have structures which have a tetrapeptide chain. Also the pharmacodynamic properties of these compounds are unexpected, especially their potent renal effects.

DESCRIPTION OF THE INVENTION

The new compounds of this invention are represented by the following structural formula:

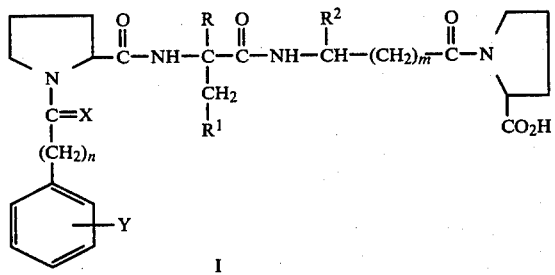

I in which:
R is hydrogen or lower alkyl of 1-3 carbons;
$R^1$ is hydrogen, phenyl or phenyl optionally substituted with 1 or 2 hydroxy or methoxy groups;
$R^2$ is hydrogen, lower alkyl of 1-3 carbons, phenyl or phenyl optionally substituted with 1 or 2 hydroxy or methoxy groups; and
Y is hydrogen, hydroxy or methoxy;
X is O or H,H; and
n and m are each integers from 0-4.

A subgeneric group of the new compounds of this invention are those represented by Formula I in which X is O; R is methyl, $R^1$ is phenyl or optionally substituted phenyl as described above and m is O.

Species of high renal activity are the compounds in which R is hydrogen or methyl, $R^1$ is phenyl, $R^2$ is hydrogen, n is 3, m is O and X is O especially in the L-prolyl-DL-α-methylphenylalanyl-glycyl-L-proline or L-prolyl-L-phenylalanyl-glycyl-L-proline configurations.

Certain of these compounds include the various pharmaceutically acceptable salt forms of the invention such as those formed with nontoxic acids due to the basic N-member of the N-phenylalkylprolyl fragment (Formula I when X is H,H) or those formed by reaction of a carboxylic acid group with pharmaceutically acceptable bases such as the alkali metal hydroxides. The former include the sulfate, hydrochloride, phosphate, hydrobromide, ethanedisulfonate, methanesulfonate and the like. The latter include the sodium, potassium, calcium salts as well as other nontoxic salts with strong organic bases. The alkali metal salts are most useful as intermediates rather than as end products although they may be used either way. The salts are formed by reacting the compounds of Formula I in a suitable solvent with an appropriate acid or base, using reaction conditions which will be readily apparent to those skilled in the art. Usually, an excess of the inorganic acid or base is reacted with the compound of this invention dissolved in water or in an appropriate organic solvent such as aqueous ethanol. The compounds of this invention often form solvates such as hydrates or lower alcoholates.

The tetrapeptides in the form of the free acids are most useful compounds of this invention.

Further the acid forms of Formula I may be used in pro-drug forms, such as a lower alkyl ester derivative of from 1-5 carbons in said alkyl group or such as a benzyl or other ester-like group.

The compounds of this invention are conveniently prepared by reaction sequences using standard peptide coupling reactions which involve as a key step the formation of the amide bond by the two dipeptide subunits. Most useful is reacting the carboxylic acid bearing fraction, (II) below, with the amine bearing fraction (III) in the presence of a dehydrating coupling agent common in the peptide art. Dicyclohexylcarbodiimide is used under conditions which employ reacting it with the dipeptide subunits in a suitable organic solvent such as tetrahydrofuran, dimethylacetamide or dimethylformamide at moderate temperatures, for example at ambient temperature.

Reaction Sequence A

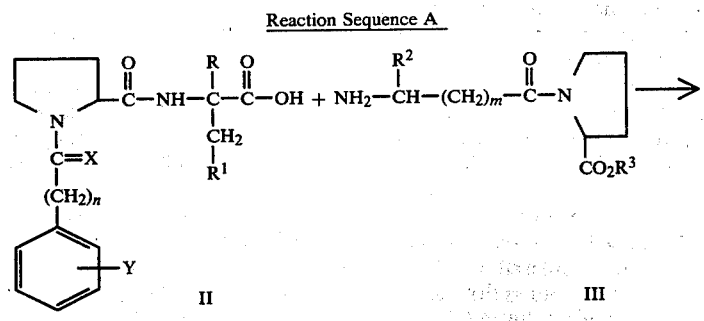

II          III

-continued

Reaction Sequence A

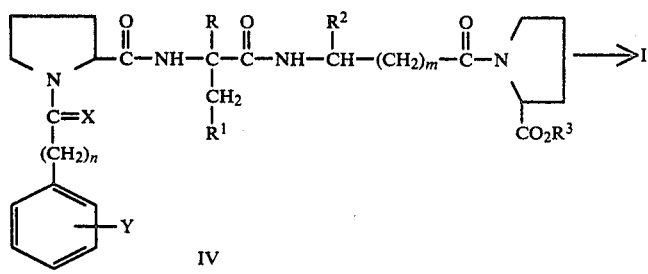

IV

In Reaction Sequence A, X, Y, n, m, R, $R^1$ and $R^2$ are as described above for the compounds of Formula I or precursors therefor, $R^3$ is an easily removed carboxylic protective group such as a benzyl or allyl group which can be removed by catalytic hydrogenation.

The carboxylic acid bearing dipeptide (II) is prepared from known starting materials by N-alkylation or N-acylation of proline or, preferably, an ester of proline as known to the art, then, condensation of the resulting compound with the desired alanine derivative using standard peptide coupling reactions. The amine bearing dipeptide (III) is prepared from known starting materials by reacting a N-protected glycine, such as t-boc. derivative, with a proline ester, followed by regeneration of the amine function.

Of course, the order of condensation in building the tetrapeptide chain may be altered as will be recognized by one skilled in the art. The condensation of two dipeptides is more convenient than is the condensation of a tripeptide with a suitable amino acid.

The chemical protective devices on any functional groups in the compounds of structure IV are then removed. For example, in the most useful route of synthesis, that is when $R^3$ in Structure IV is an ester forming group susceptible to removal by catalytic hydrogenation such as benzyl or a substituted benzyl group, the intermediate compound is treated in an organic solvent such as methanol or ethanol over a palladium catalyst under moderate hydrogenation conditions to give the desired end product of this invention. The tetrapeptide products of this invention are also prepared using solid phase or enzyme technology commonly used in preparing peptides, R. B. Merrifield, Biology 3 1385 (1964) and J. Am. Chem. Soc. 85 2149 (1963).

The compounds of this invention have renal pharmacodynamic activity and, as such, are useful pharmaceutical compounds. More specifically, their renal effects are similar to those of dopamine but at very low doses. Their improvement of kidney function often appears to be cumulative. These compounds, therefore, are relatively long acting agents for improving kidney function and, thereby, for treating hypertension in patients in need of such treatment.

The biological activity of the compounds of Formula I was demonstrated by administering the compounds by infusion to anesthetized dogs measuring the mean arterial blood pressure (MAP), renal blood flow (RBF), renal vascular resistance (RVR) and heart rate (HR) in the test procedure explained in detail in U.S. Pat. No. 4,197,297. Generally speaking, the compounds demonstrated a decreased renal vascular resistance and increased renal blood flow at doses ranging from one half to one hundred times of that for dopamine in this test procedure. Specific results demonstrating this biological utility are included in the examples.

The new chemical compounds described above are incorporated into dosage unit forms and used in methods for improving renal function and, thereby, treating high blood pressure.

The pharmaceutical compositions of this invention having peripheral dopaminergic-like, or, more specifically, renal function improvement activity are prepared in conventional dosage unit forms by incorporating a compound of Formula I, an isomer thereof, a pharmaceutically acceptable salt thereof or a prodrug derivative thereof with a nontoxic pharmaceutical carrier according to accepted pharmaceutical procedures in a nontoxic amount sufficient to produce the desired pharmacodynamic activity in an animal or human subject. Preferably, the compositions will contain the active ingredient in an active but nontoxic amount selected from about 5 mg to about 500 mg, preferably about 25-100 mg, of active ingredient per dosage unit. This quantity will vary depending on the relative potency of the basic compound, the specific biological activity desired, the route of administration and the conditions of the patient.

The methods of using the new compounds of this invention for medical purposes manifest themselves in a number of ways. Broadly speaking, a peripheral dopamine-like effect in the form of a specific renal vasodilation is produced in patients in need thereof. The compounds induce an increased renal blood flow, usually at a low dose compared with similar peptides in my earlier patent application referred to above. The end result will be an anti-hypertensive effect and improved renal function. This assertion does not rule out that the described end result may be wholly or partially due to another mechanism of action, one unlike that of dopamine.

Alternatively, since the compounds of this invention are selective peripheral dopaminergic-like compounds and dopamine itself is useful in the treatment of shock, these compounds, for example the compound of Example 1 below, may be used to treat shock in the hospital or emergency treatment room when administered intravenously at a dose selected from the range of about 10-200 mcg/min of the basic compound for the average human subject. Dopamine, itself, in the dog test procedure outlined above has an $ED_{15}$ of about 3 mcg/kg/min. In medical practice, dopamine has utility for treating various hemodynamic imbalances as noted in the Physicians' Desk Reference 33 566 (1977) but such uses are not renally selective.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly, the carrier or diluent may include any time delay material well known in the art, such as glyceryl monostearate of glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed. Thus, if a solid carrier for oral administration is used, the active ingredient can be tableted, placed in a hard gelatin capsule in powder, regular or sustained release pellet form or placed in the form of a troche or lozenge. The amount of solid carrier will vary widely but, preferably, will be from about 25 mg to about 1 g. If a liquid carrier is used, the preparation will be in the form of a syrup, emulsion, soft gelatin capsule, sterile injectable liquid such as in an ampul together with an aqueous or nonaqueous liquid suspension for oral administration.

The pharmaceutical preparations are made following the conventional techniques of the pharmaceutical chemist involving mixing, granulating and compressing, when necessary, or variously mixing and dissolving the ingredients as appropriate to give the desired dosage unit.

The method of producing dopaminergic-like activity in accordance with this invention comprises administering internally to a subject in need of such activity a nontoxic amount, sufficient to produce said activity, of a compound of Formula I or a pharmaceutically acceptable salt or prodrug thereof, usually combined with a pharmaceutical carrier. The route of administration may be any route which effectively transports the active compound to the kidney receptors which are to be stimulated. Oral or parenteral administration are preferred. Advantageously, equal doses within the ranges given above will be administered several times, such as from two to five times, a day with the daily dosage regimen being selected from a range of about 10 mg to about 1.0 g, preferably 50–500 mg/kg, for oral dosage units. When the method described above is carried out, anti-hypertensive activity and improved renal function are produced with a minimum of central nervous system or cardiac side effects. For treating an average size human patient using the preferred compound mentioned above, a dose to improve renal function would be selected from the range of from about 15–75 mg for each dosage unit adapted for oral administration said dose to be administered from 2–5 times daily. An equivalent amount injected parenterally in dosage units or by infusion is also useful.

One skilled in the art will recognize that the compounds of this invention may exist in various configurations such as optical isomers or mixtures thereof. Isomeric compounds other than those specifically described here are easily prepared by substituting the amino acid of a selected configuration into the chemical reactions of the examples which illustrate this invention. Also the proline rings in the compounds of Formula I may be replaced by other prolyl-like fragments such as dehydroprolyl,

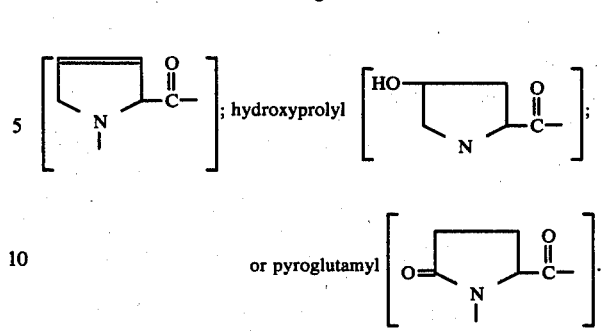

The following examples are intended to teach the preparation and use of the new compounds of this invention but not to limit its scope. All temperatures are expressed in degree Centigrade.

EXAMPLE 1

A mixture of 3.5 g (0.02 m) of N-tert.butoxycarbonyl-glycerine, 5.4 g (0.04 m) of 1-hydroxybenzotriazole, 4.82 g (0.02 m) of proline, benzyl ester hydrochloride, 6 ml of N-ethylmorpholine and 50 ml of dry tetrahydrofuran was mixed with 4.12 g (0.02 m) of dicyclohexylcarbodiimide at 10° then was stirred for ½ hour in the cold and at room temperature for 17 hours. The mixture was filtered. The filtrate was evaporated and partitioned between ice water, dilute hydrochloric acid and ethyl acetate. The organic extract was washed with dilute hydrochloric acid, water, bicarbonate and brine. The dried extract was concentrated to leave 7.2 g of syrupy N-t-boc.-glycyl-L-proline, benzyl ester.

This material (7.2 g) was stirred in 40 ml of methylene chloride and 15 ml of trifluoroacetic acid at room temperature for 3 hours. The mixture was evaporated. The residue was taken up in ether, acidified with ethereal hydrogen chloride and diluted with ether to give a glassy glycyl-L-proline benzyl ester as the hydrochloride salt. Thin layer analysis demonstrated one product only.

A mixture of 15.13 g (0.0626 m) of L-proline benzyl ester hydrochloride, 11.3 g (0.0628 m) of 4-(4-hydroxyphenyl)-butyric acid, 17.0 g (0.126 m) of 1-hydroxybenzotriazole, 12.0 ml of N-ethylmorpholine, 40 ml of dimethylformamide, 80 ml of tetrahydrofuran and 13.0 g (0.063 m) of dicyclohexylcarbodiimide was stirred for 3 hours at room temperature. The mixture was filtered and the tetrahydrofuran removed in vacuo from the filtrate. The residue was then diluted with water and ethyl acetate. The resulting mixture was acidified with dilute hydrochloric acid. The layers were separated. The organic layer was extracted several times with ethyl acetate. The organic extracts were washed with dilute acid, water, bicarbonate solution and brine then dried and evaporated to give a syrup which was taken through a silica gel column with methylene chloride then 1% methanol in methylene chloride to give 18.9 g (83%) of N-4-(4-hydroxyphenyl)-butyrylproline benzyl ester, m/e=367.

This material (18.9 g, 0.051 m) was dissolved in 100 ml of ethyl alcohol and hydrogenated over 2.5 g of 10% palladium-on-charcoal. The mixture was filtered and the filtrate evaporated to give 15 g of the desired free acid, m/e 277.

The N-acylproline (2.8 g, 0.01 m) was mixed with 2.9 g (0.01 m) of D,L-α-methyl-3,4-dimethoxyphenylalanine methyl ester hydrochloride, 2.7 g (0.02 m) of 1- hydroxybenzotriazole, 2.0 ml of N-ethylmorpholine, 2.06 g (0.01 m) of dicyclohexylcarbodiimide, 20 ml of dimethylformamide and 40 ml of tetrahydrofuran. The mixture was stirred at room temperature for 72 hours.

The reaction mixture was filtered. The filtrate was concentrated. The residue was taken up in ethyl acetate and washed with dilute acid, water, bicarbonate and brine. The organic extract was dried and evaporated to give 5.12 g of N-4-(4-hydroxyphenyl)-butyryl-L-prolyl-D,L-α-methyl-3,4-dimethoxyphenylalanine methyl ester, m/e 512.

The ester dipeptide (5.0 g, 9.77 mm), 45 ml of methyl alcohol and 2.5 ml of 2.5 N sodium hydroxide solution were mixed and stirred for 17 hours. The methanol was taken off and the residue taken up in water and filtered. The aqueous solution was acidified with conc. hydrochloric acid to give a solid which was taken into methylene chloride. After washing with water, the methylene chloride extract was dried and evaporated to give 3.2 g of the desired dipeptide intermediate as the free acid, m/e 498.

Dicyclohexylcarbodiimide (1.28 g, 6.2 mm) is added to a mixture of 3.1 g (6.2 mm) of the dipeptide acid, 1.87 of glycyl-L-proline benzyl ester, 12.4 mm of 1-hydroxybenzotriazole, 3.0 ml of N-ethylmorpholine, 10 ml of dimethylformamide and 30 ml of dry tetrahydrofuran. The resulting mixture is stirred at room temperature for 54 hours. The mixture is filtered and the filtrate diluted with iced brine, dilute hydrochloric acid and ethyl acetate. The organic extract is washed as above, dried and evaporated to give N-4-(4-hydroxyphenyl)-butyryl-L-prolyl-D,L-α-methyl-3,4-dimethoxyphenylalanyl-glycyl-L-prolyl benzyl ester.

A mixture of 1.75 g of the ester acid, 2.5 g of 10% palladium-on-barium sulfate, 50 ml of ethyl alcohol and 30 ml of glacial acetic acid is hydrogenated at low pressure. The catalyst is removed by filtration and the hydrogenation solution is evaporated. The residue is recrystallized to give N-4-(4-hydroxyphenyl)-butyryl-L-propyl-D,L-α-methyl-3,4-dimethoxyphenylalanyl-glycyl-L-proline.

The sodium salt is prepared by stirring a solution of the free acid in 4:1 ether-methanol with a slight excess of a solution of sodium 2-ethyl hexanoate in 2-propanol, or by titrating a solution of the free acid dissolved in ethyl acetate with a 5% solution of sodium methoxide in methanol to pH 7 followed by precipitation of the sodium salt with ether/petroleum ether.

EXAMPLE 2

Using the method of Example 1, 6.93 g (0.025 m) of N-4-(4-hydroxyphenyl)-butyryl-L-proline was condensed with 5.74 g (0.025 m) of D,L-α-methylphenylalanine methyl ester hydrochloride to give, after hydrolysis, 8.35 g of N-4-(4-hydroxyphenyl)-butyryl-L-prolyl-D,L-α-methylphenylalanine, m/e 438.

This compound (1.43 g, 3.25 mm) was reacted with 2.99 g (10 m) of glycyl-L-proline benzyl ester by hydrochloride prepared as in Example 1 along with 1.35 g of 1-hydroxybenzotriazole, 5 ml of N-ethylmorpholine and 1.03 g of dicyclohexylcarbodiimide and 50 ml of dry tetrahydrofuran at room temperature for 60 hours. The material was worked up as in Example 1 to give 3.4 g of white solid.

This material was taken over a silica gel column using methylene chloride→methanol:methylene chloride to give 1.6 g (72%) of 4-(4-hydroxyphenyl)-butyryl-L-prolyl-D,L-α-methylphenylalanyl-glycyl-L-proline benzyl ester; mass spectrum analysis gave a molecular weight of 682 with a consistent pattern.

A mixture of 1.5 g (2.2 mm) of the benzyl ester, 50 ml of ethanol, 50 ml of glacial acetic acid and 1.2 g of 10% palladium-on-carbon was shaken on a low pressure hydrogenation apparatus for six hours. The catalyst was removed. The filtrate was evaporated to leave a residue which was azeotroped with ethanol, toluene and ethanol again. The solid product (1.1 g, 85%) was white amorphous 4-(4-hydroxyphenyl)-butyryl-L-propyl-D,L-α-methylphenylalanyl-glycyl-L-proline, m.p. 115°–117° after drying at 56°, $[\alpha]_D^{25} = -78.9°$ in methanol.

Anal. Calcd. for $C_{32}H_{40}N_4O_7 \cdot H_2O$: C, 62.94; H, 6.93; N, 9.17. Found: C, 62.67, 62.37; H, 6.92, 7.19; N, 8.74, 8.60.

In the anesthetized dog protocol discussed above this compound gave the following data:

| | Dose (μg/kg/min) | % change in 1 dog | | | |
|---|---|---|---|---|---|
| | | MAP | RBF | RVR | HR |
| Dopamine | 3 | −16 | 28 | −34 | 2 |
| Tetrapeptide | 3.0 | −5 | 17 | −18 | 6 |
| | 30 | −9 | 16 | −21 | 10 |
| | 300 | −6 | 14 | −17 | 6 |

In the cumulative effect of the test compound, that is, the effect measured after the normal period of the test, the cardiac rate (HR) decreased from a predrug level of 140 BPM to 105 BPM. Renal blood flow increased from 127 ml/min to 162 ml/min.

In a secondary test, the tetrapeptide demonstrated an $ED_{15}$ of 1.9 μg/kg with dopamine having an $ED_{15}$ of 3.5 μg/kg.

The tetrapeptide was not active in the spontaneously hypertensive rat protocol except for a slight water diuresis. It was also inactive in the toad bladder test for reversal of antidiuretic hormone activity.

This compound (125 mg) is filled into a hard gelatin capsule and administered from 3–5 times daily orally to a patient in need of improved kidney function. It is also dissolved in saline and administered by infusion at a rate of 1.5 μg/kg/min.

EXAMPLE 3

Hydrogen chloride gas was passed through a mixture of 10 g of D-phenylalanine and 150 ml of dry methanol at 0° for 2 hours. The mixture was evaporated slowly under vacuum. The residue was redissolved in 150 ml of dry methanol and re-saturated with hydrogen chloride at 0° for 2 hours. Again the solvents were evaporated and the residue triturated with ether to give a white solid which was recrystallized from methanol:ether to give 7.2 g of the methyl ester of D-phenylalanine as the hydrochloride salt, m.p. 158°–160°, $[\alpha]_D^{25} = -16°$ in methanol.

A mixture of 3.71 g (0.134 m) of N-4-(4-hydroxyphenyl)-butyryl-L-proline, 2.89 g (0.0134 m) of the methyl ester of D-phenylalanine, 3.62 g (0.0268 m) of 1-hydroxybenzotriazole, 5 ml of N-ethylmorpholine, 2.76 g (0.0134 m) of dicyclohexylcarbodiimide and 75 ml of dry tetrahydrofuran was reacted at 25° for 17 hours. Working up as described above gave 6.19 of N-4-(4-hydroxyphenyl)-butyryl-L-prolyl-D-phenylalanine, methyl ester, m/e 438.

This ester (6.0 g, 0.0137 m) was hydrolyzed by using a solution of 75 ml of methanol and 25 ml of 2.5 N sodium hydroxide solution at 25° for 17 hours. The methanol was evaporated and the residue was dissolved in water. The mixture was filtered. The filtrate was acidified with concentrated hydrochloric acid to give a white solid which was extracted with ethyl acetate. After washing with water, the dried extract was evaporated to give 5.4 g of N-4-(4-hydroxyphenyl)-butyryl-L-prolyl-D-phenylalanine, m/e 424.

This material (3.18 g, 0.0075 m) was reacted with 2.25 g (0.0075 m) of glycyl-L-proline, benzyl ester hydrochloride using the dicyclohexylcarbodiimide procedure described above at 25° for 17 hours. After working up as described, the residue was purified over a 180 g column of silica gel to give 2.7 g (54%) of amorphous N-4-(4-hydroxyphenyl)-butyryl-L-prolyl-D-phenylalanyl-glycyl-L-proline, benzyl ester, m/e 668.

The ester (2.6 g, 3.9 mm) in aqueous methanol was hydrogenated as described to give 1.8 g (80%) of N-4-(4-hydroxyphenyl)-butyryl-L-prolyl-D-phenylalanyl-glycyl-L-proline, m.p. 118°-120°.

Anal. Calcd. for $C_{31}H_{38}N_4O_7 \cdot \frac{1}{2}H_2O$: C, 63.36; H, 6.69; N, 9.53. Found: C, 63.43; H, 6.92; N, 9.05, $[\alpha]_D^{25} = -38.0°$ in methanol.

This compound at 300 μg/kg/min in the anesthetized dog gave the following cumulative effects: MAP, 0; RBF, +22; RVR, −18; HR, −8.

EXAMPLE 4

The procedure of Example 2 was used to condense 2.77 g (0.01 m) of N-4-(4-hydroxyphenyl)-butyryl-L-proline with 2.46 g (0.01 m) of D,L-α-methyltyrosine, methyl ester to give the dipeptide 4-(4-hydroxyphenyl)-butyryl-L-prolyl-D,L-α-methyltyrosine methyl ester (4.8 g m/e 468). Saponification of 6.0 g of the ester gave the free acid, m/e 454 (5.4 g) which (2.5 g, 0.0055 m) was condensed with 2.0 g (0.0066 m) of glycyl-L-proline, benzyl ester hydrochloride using dicyclohexylcarbodiimide to give N-4-(4-hydroxyphenyl)-butyryl-L-prolyl-D,L-α-methyltyrosyl-glycyl-L-proline benzyl ester after silica gel chromatography, 4.3 g, m/e 698 and 699, separation of the D and L isomers was observed upon chromatography. The protective benzyl group was removed by hydrogenation as described using 1.5 g (2.2 mm) of ester in 80 ml of ethanol-glacial acetic acid to give N-4-(4-hydroxyphenyl)-butyryl-L-prolyl-D,L-α-methyltyrosyl-glycyl-L-proline, 1.18 g, m.p. 117°-122°, $[\alpha]_D^{25} = -64.7°$.

Anal. Calcd. for $C_{32}H_{40}N_4O_8 \cdot C_2H_5OH$: C, 62.37; H, 7.08; N, 8.56. Found: C, 62.12; H, 7.18; N, 8.03.

This compound (150 mg) in dosage unit form is administered three times daily to a patient in need of renal function improvement.

EXAMPLE 5

The chemical methods of Example 2 are used starting with N-(2-phenyl)-ethanoyl-D,L-proline to give N-(2-phenyl)-ethanoyl-D,L-proline-D,L-α-methylphenylalanyl-glycyl-L-proline, using D,L-phenylglycine instead of glycine gives N-4-(4-hydroxyphenyl)-butyryl-L-proline-DL-α-methylphenylalanyl-D,L-phenylglycyl-L-proline. Using alanine in Example 2 in place of glycine gives N-4-(4-hydroxyphenyl)-butyryl-L-proline-D,L-α-methylphenylalanyl-alanyl-L-proline. Using N-benzyl-L-proline, prepared by reacting proline benzyl ester with benzyl bromide in pyrimidine, gives N-benzyl-L-prolyl-D,L-α-methylphenylalanyl-glycyl-L-proline as the sulfate salt. N-4-(4-hydroxyphenyl)butyryl-D-prolyl-L-phenylalanyl-glycyl-D-proline is also prepared in similar fashion.

What is claimed is:

1. A chemical compound of the structural formula:

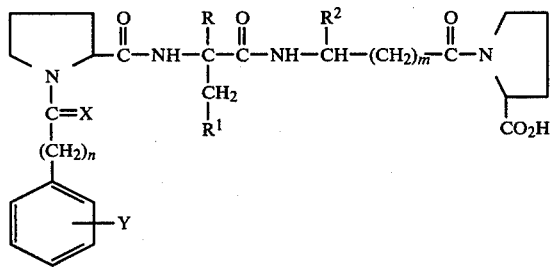

in which:

R is hydrogen or lower alkyl of 1-3 carbons;
$R^1$ is hydrogen, phenyl or phenyl optionally substituted by 1 or 2 hydroxy or methoxy groups;
$R^2$ is hydrogen, lower alkyl of 1-3 carbons, phenyl or phenyl optionally substituted by 1 or 2 hydroxy or methoxy groups;
Y is hydrogen, hydroxy or methoxy;
X is O or H,H; and
n and m are each integers of from 0-4; or pharmaceutically acceptable acid addition or alkali metal salts thereof.

2. The compound of claim 1 in which X is O.

3. The compound of claim 1 in which X is O and R is methyl.

4. The compound of claim 1 in which X is O, n is 3, m is O.

5. The compound of claim 1 in which X is O, n is 3, m is O and the configuration of the two prolyl units is L.

6. The compound of claim 1 being N-4-(4-hydroxyphenyl)-butyryl-L-prolyl-D,L-α-methylphenylalanyl-glycyl-L-proline.

7. The compound of claim 1 being N-4-(4-hydroxyphenyl)-butyryl-L-prolyl-D,L-α-methyl-3,4-dimethoxyphenylalanyl-glycyl-L-proline.

8. The compound of claim 1 being N-4-(4-hydroxyphenyl)-butyryl-L-prolyl-D-phenylalanyl-glycyl-L-proline.

9. The compound of claim 1 being N-4-(4-hydroxyphenyl)-butyryl-L-prolyl-L-phenylalanyl-glycyl-L-proline or its alkali metal salts.

10. The compound of claim 1 being N-4-(4-hydroxyphenyl)-butyryl-L-prolyl-D,L-α-methyltyranosyl-glycyl-L-proline.

11. The method of improving kidney function in a subject in need thereof comprising administering orally or parenterally to said subject a nontoxic, therapeutically effective quantity of a compound of claims 1, 2, 3, 4, 5, 6, 7, 8, 9 or 10.

12. The pharmaceutical composition effective for improving kidney function comprising a nontoxic, therapeutically effective quantity of a compound of claims 1, 2, 3, 4, 5, 6, 7, 8, 9 or 10 and a carrier therefor.

* * * * *